(12) United States Patent
Tan et al.

(10) Patent No.: US 11,439,340 B2
(45) Date of Patent: Sep. 13, 2022

(54) DISPLAY DEVICES AND METHODS FOR CONTROLLING A DISPLAY DEVICE

(71) Applicant: RAZER (ASIA-PACIFIC) PTE. LTD., Singapore (SG)

(72) Inventors: Min-Liang Tan, Singapore (SG); Kian Sin Yeo, Singapore (SG); Beng Leong Toh, Singapore (SG); Ji Fong Lim, Singapore (SG); Gui Mei Dai, Singapore (SG); Kah Yong Lee, Singapore (SG); Aninda Kanti Sen, Singapore (SG)

(73) Assignee: Razer (Asia-Pacific) Pte. Ltd., Singapore (SG)

( * ) Notice: Subject to any disclaimer, the term of this patent is extended or adjusted under 35 U.S.C. 154(b) by 687 days.

(21) Appl. No.: 16/308,809

(22) PCT Filed: Jun. 17, 2016

(86) PCT No.: PCT/SG2016/050279
§ 371 (c)(1),
(2) Date: Dec. 10, 2018

(87) PCT Pub. No.: WO2017/217928
PCT Pub. Date: Dec. 21, 2017

(65) Prior Publication Data
US 2019/0307351 A1 Oct. 10, 2019

(51) Int. Cl.
*A61B 5/375* (2021.01)
*A63F 13/212* (2014.01)
(Continued)

(52) U.S. Cl.
CPC ............ *A61B 5/375* (2021.01); *A61B 5/0006* (2013.01); *A61B 5/1123* (2013.01); *A61B 5/165* (2013.01);
(Continued)

(58) Field of Classification Search
CPC ......... A61B 5/165; A61B 5/375; A61B 5/291; A61B 5/396; A61B 5/316; A61B 5/0006;
(Continued)

(56) References Cited

U.S. PATENT DOCUMENTS 6,450,820 B1 * 9/2002 Palsson ................... G09B 19/22
434/236
8,556,951 B2 10/2013 Witt et al.
(Continued)

FOREIGN PATENT DOCUMENTS

CN 1719385 A 1/2006
CN 102438063 A 5/2012
(Continued)

OTHER PUBLICATIONS

Extended European Search Report dated Apr. 16, 2019, 7 pages, for the corresponding European Patent Application No. 16905622.3.
(Continued)

*Primary Examiner* — Patrick Fernandes
(74) *Attorney, Agent, or Firm* — Polsinelli PC

(57) ABSTRACT

According to various embodiments, a display device may be provided. The display device may include: a receiver configured to receive user data based on an electroencephalography measurement; at least one light source; and a controller configured to control the at least one light source based on the user data.

19 Claims, 2 Drawing Sheets

(51) Int. Cl.
  *A63F 13/42*   (2014.01)
  *A61B 5/00*    (2006.01)
  *A61B 5/11*    (2006.01)
  *A61B 5/16*    (2006.01)
  *G06F 3/01*    (2006.01)
  *A61M 21/00*   (2006.01)
  *A61B 5/316*   (2021.01)

(52) U.S. Cl.
  CPC ............ *A61B 5/316* (2021.01); *A61B 5/6803* (2013.01); *A61B 5/7445* (2013.01); *A61M 21/00* (2013.01); *A63F 13/212* (2014.09); *A63F 13/42* (2014.09); *G06F 3/015* (2013.01); *A61B 2503/12* (2013.01); *A61M 2021/0044* (2013.01); *A61M 2205/3553* (2013.01); *A61M 2205/3561* (2013.01); *A61M 2205/502* (2013.01); *A61M 2205/584* (2013.01); *A61M 2205/587* (2013.01); *A61M 2230/10* (2013.01); *A63F 2300/1012* (2013.01); *A63F 2300/6045* (2013.01)

(58) Field of Classification Search
  CPC ... A61B 5/1123; A61B 5/6803; A61B 5/7445; A61B 2503/12; A63F 3/10; A63F 13/212; A63F 13/42; A63F 2300/1012; A63F 2300/6045; G06F 3/015; A61M 2021/0044; A61M 2205/3553; A61M 2205/3561; A61M 2205/502; A61M 2205/584; A61M 2205/587; A61M 2230/10
  See application file for complete search history.

(56) References Cited

U.S. PATENT DOCUMENTS

| | | | |
|---|---|---|---|
| 9,118,775 B2 | 8/2015 | Lim et al. | |
| 9,211,077 B2 | 12/2015 | Jung et al. | |
| 9,531,859 B2 | 12/2016 | Tan et al. | |
| 2008/0177197 A1 | 7/2008 | Lee et al. | |
| 2008/0183081 A1 | 7/2008 | Lys et al. | |
| 2009/0312998 A1 | 12/2009 | Berckmans et al. | |
| 2010/0240458 A1 | 9/2010 | Gaiba et al. | |
| 2012/0052905 A1 | 3/2012 | Lim et al. | |
| 2012/0083668 A1* | 4/2012 | Pradeep | A61B 5/4809 600/300 |
| 2013/0138182 A1 | 5/2013 | Nissila et al. | |
| 2014/0035818 A1* | 2/2014 | Matsuoka | G06F 1/3231 345/168 |
| 2014/0276183 A1 | 9/2014 | Badower | |
| 2014/0316230 A1 | 10/2014 | Denison et al. | |
| 2014/0330408 A1* | 11/2014 | Rolley | G06K 9/00288 700/91 |
| 2015/0092972 A1 | 4/2015 | Lai et al. | |
| 2015/0204561 A1 | 7/2015 | Sadwick et al. | |
| 2015/0248470 A1 | 9/2015 | Coleman et al. | |
| 2016/0119463 A1 | 4/2016 | Tan et al. | |

FOREIGN PATENT DOCUMENTS

| | | |
|---|---|---|
| CN | 105339864 A | 2/2016 |
| CN | 106020507 A | 9/2019 |
| KR | 10-1373058 B1 | 3/2014 |
| KR | 10-2015-0115524 A | 10/2015 |
| KR | 10-1907090 B1 | 10/2018 |
| TW | M374844 U | 3/2010 |
| WO | WO 2014/085910 A1 | 6/2014 |
| WO | WO 2015/010920 A1 | 1/2015 |
| WO | WO 2015/113003 A1 | 7/2015 |
| WO | WO 2015/122846 A1 | 8/2015 |
| WO | WO 2015/177500 A1 | 11/2015 |

OTHER PUBLICATIONS

Office Action (including English Translation) dated Apr. 20, 2021, for the corresponding Taiwanese Application No. 106119807 in 19 total pages.

Office Action (including English Translation) dated Oct. 14, 2020, for the corresponding Taiwanese Application No. 106119807 in 20 total pages.

International Search Report and Written Opinion, dated Mar. 17, 2017, for the corresponding International Application No. PCT/SG2016/050279 in 11 pages.

Office Action (including English Translation) dated Jun. 28, 2021, for the corresponding Chinese Application No. 201680088265.9 in 18 total pages.

Office Action (including English Translation) dated Jul. 26, 2021, for the corresponding Taiwanese Application No. 106119807 7 in 27 total pages.

* cited by examiner

DISPLAY DEVICES AND METHODS FOR CONTROLLING A DISPLAY DEVICE

TECHNICAL FIELD

Various embodiments generally relate to display devices and methods for controlling a display device.

BACKGROUND

For example during computer gaming, it may be interesting for an audience to gain insight into the mental state of a player. As such, there may be a need for devices and methods which give an indication of a player's mental state in an easy to observe way.

SUMMARY OF THE INVENTION

According to various embodiments, a display device may be provided. The display device may include: a receiver configured to receive user data based on an electroencephalography measurement; at least one light source; and a controller configured to control the at least one light source based on the user data.

According to various embodiments, a method for controlling a display device may be provided. The method may include: receiving user data based on an electroencephalography measurement; and controlling at least one light source of the display device based on the user data.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. The dimensions of the various features or elements may be arbitrarily expanded or reduced for clarity. In the following description, various embodiments of the invention are described with reference to the following drawings, in which.

DETAILED DESCRIPTION

Figure 1A:
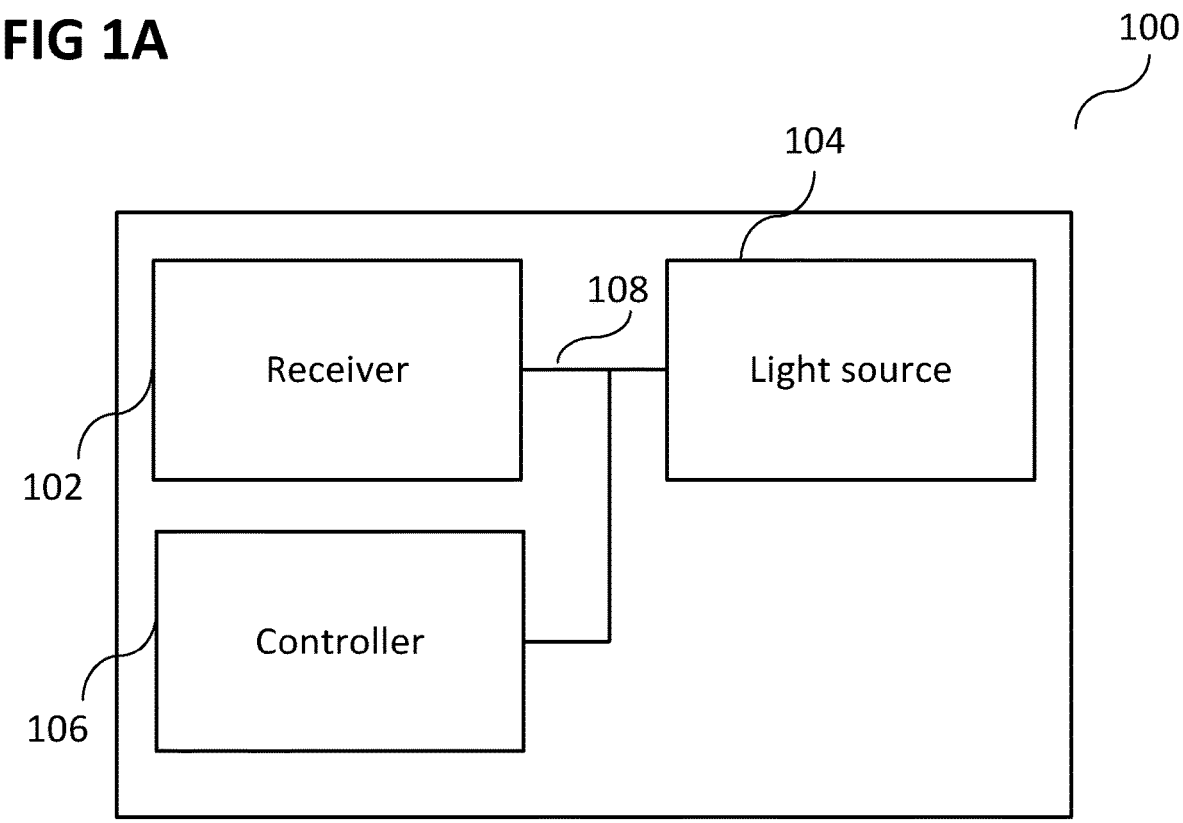
FIG. 1A shows a display device according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In this context, the display device as described in this description may include a memory which is for example used in the processing carried out in the display device. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

In the specification the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

The reference to any prior art in this specification is not, and should not be taken as an acknowledgement or any form of suggestion that the referenced prior art forms part of the common general knowledge in Australia (or any other country).

In order that the invention may be readily understood and put into practical effect, particular embodiments will now be described by way of examples and not limitations, and with reference to the figures.

Various embodiments are provided for devices, and various embodiments are provided for methods. It will be understood that basic properties of the devices also hold for the methods and vice versa. Therefore, for sake of brevity, duplicate description of such properties may be omitted.

It will be understood that any property described herein for a specific device may also hold for any device described herein. It will be understood that any property described herein for a specific method may also hold for any method described herein. Furthermore, it will be understood that for any device or method described herein, not necessarily all the components or steps described must be enclosed in the device or method, but only some (but not all) components or steps may be enclosed.

The term "coupled" (or "connected") herein may be understood as electrically coupled or as mechanically coupled, for example attached or fixed, or just in contact without any fixation, and it will be understood that both direct coupling or indirect coupling (in other words: coupling without direct contact) may be provided.

For example during computer gaming, it may be interesting for an audience to gain insight into the mental state of a player. According to various embodiments, devices and methods may be provided which give an indication of a player's mental state in an easy to observe way.

According to various embodiments, a mental state indication via a light source (for example via LEDs (light emitting diodes) or any similar light emitting devices) may be provided.

FIG. 1A shows a display device 100 according to various embodiments. The display device 100 may include a receiver 102 configured to receive user data based on an electroencephalography measurement. The display device 100 may further include at least one light source 104. The display device 100 may further include a controller 106 configured to control the at least one light source based on the user data. The receiver 102, the at least one light source 104, and the controller 106 may be coupled with each other, like indicated by lines 108, for example electrically coupled, for example using a line or a cable, and/or mechanically coupled.

In other words, a display device 100 may indicate data indicating an electroencephalography measurement received from external to the display device 100.

According to various embodiments, the user data may include or may be or may be included in raw electroencephalography measurement data.

Figure 1B:
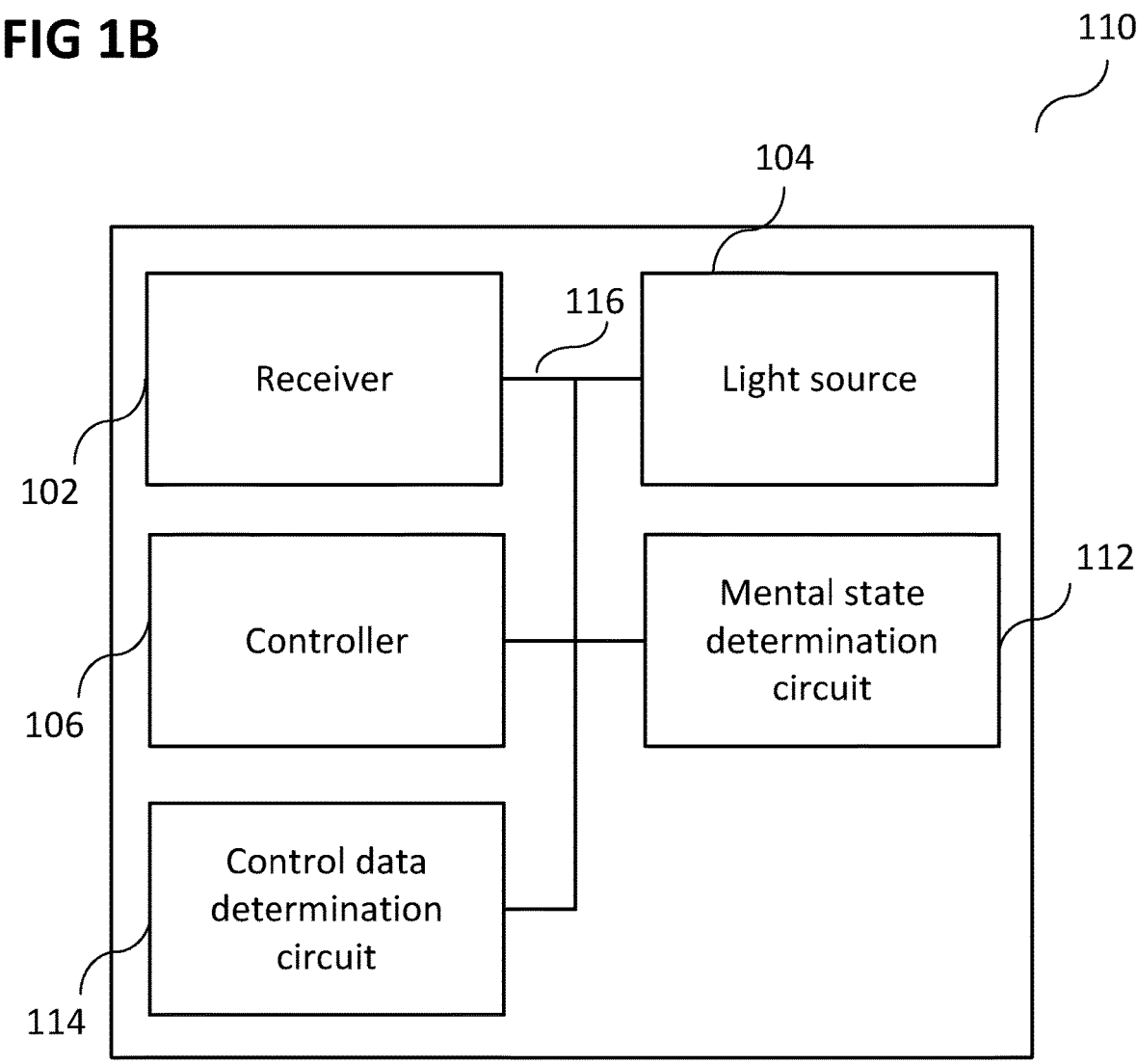
FIG. 1B shows a display device according to various embodiments.

FIG. 1B shows a display device 110 according to various embodiments. The display device 110 may, similar to the display device 100 shown in FIG. 1A, include a receiver 102 configured to receive user data based on an electroencephalography measurement. The display device 110 may, similar to the display device 100 shown in FIG. 1A, further include at least one light source 104. The display device 110 may, similar to the display device 100 shown in FIG. 1A, further include a controller 106 configured to control the at least one light source based on the user data. The display device 110 may further include a mental state determination circuit 112, like will be described in more detail below. The display device 110 may further include a control data determination circuit 114, like will be described in more detail below. The receiver 102, the at least one light source 104, the controller 106, the mental state determination circuit 112, and the control data determination circuit 114 may be coupled with each other, like indicated by lines 116, for example electrically coupled, for example using a line or a cable, and/or mechanically coupled.

According to various embodiments, the mental state determination circuit 112 may be configured to determine at least one of a mental state or a motor state based on the raw electroencephalography measurement data.

According to various embodiments, the at least one of mental state or motor state may include or may be meditative, calm, attentive, focused, winking, blinking, smiling, frowning, clenching, laughing, smiling, excited, frustrated, and/or bored.

According to various embodiments, the control data determination circuit 114 may be configured to determine control data for controlling the at least one light source based on the at least one of mental state or motor state.

According to various embodiments, the user data may include or may be or may be included in data indicating at least one of a mental state or a motor state.

According to various embodiments, the at least one of mental state or motor state may include or may be meditative, calm, attentive, focused, winking, blinking, smiling, frowning, clenching, laughing, smiling, excited, frustrated, and/or bored.

According to various embodiments, the control data determination circuit 114 may be configured to determine control data for controlling the at least one light source based on the at least one of mental state or motor state.

According to various embodiments, the user data may include or may be or may be included in control data for controlling the at least one light source.

According to various embodiments, the display device 110 may include or may be or may be included in a wearable device.

According to various embodiments, the wearable device may include or may be or may be included in at least one of a wrist band or a watch.

According to various embodiments, the display device 110 may include or may be or may be included in a peripheral device.

According to various embodiments, the peripheral device may include or may be or may be included in at least one of a mouse, a keyboard, a game controller, a headset device, a speaker device, a headset device, a head mounted device, a virtual reality device, or an augmented reality device.

According to various embodiments, the receiver 102 may include or may be at least one of a wired interface, a wireless interface, a Bluetooth interface, a ZigBee interface, an infrared interface, a wireless local area network interface, a Universal Serial Bus interface, or a Thunderbolt interface.

According to various embodiments, the at least one light source 104 may include or may be at least one colored light source. According to various embodiments, the controller 106 may be configured to control a color of the at least one light source 104 based on the user data. According to various embodiments, a plurality of colored light sources may be provided, for example in a Chroma device. According to various embodiments, both light color and light intensity may be controlled.

Figure 2:
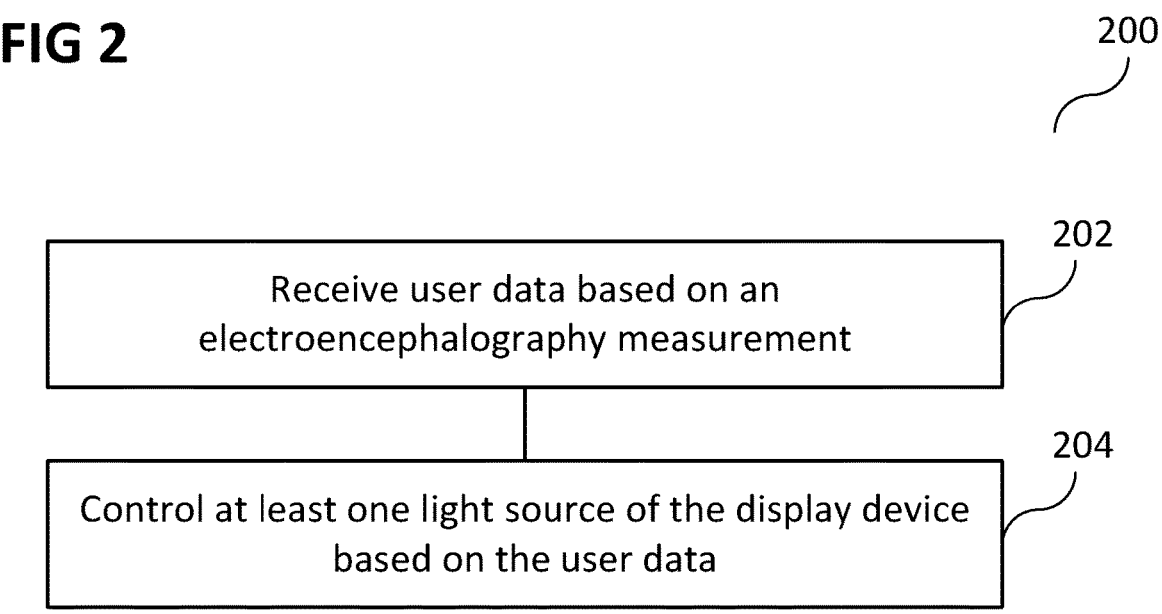
FIG. 2 shows a flow diagram illustrating a method for controlling a display device according to various embodiments.

FIG. 2 shows a flow diagram 200 illustrating a method for controlling a display device according to various embodiments. In 202, user data based on an electroencephalography measurement may be received. In 204, at least one light source of the display device may be controlled based on the user data.

According to various embodiments, the user data may include or may be or may be included in raw electroencephalography measurement data.

According to various embodiments, the method may further include determining at least one of a mental state or a motor state based on the raw electroencephalography measurement data.

According to various embodiments, the at least one of mental state or motor state may include or may be at least one of meditative, calm, attentive, focused, winking, blinking, smiling, frowning, clenching, laughing, smiling, excited, frustrated, or bored.

According to various embodiments, the method may further include determining control data for controlling the at least one light source based on the at least one of mental state or motor state.

According to various embodiments, the user data may include or may be or may be included in data indicating at least one of a mental state or a motor state.

According to various embodiments, the at least one of mental state or motor state may include or may be at least one of meditative, calm, attentive, focused, winking, blinking, smiling, frowning, clenching, laughing, smiling, excited, frustrated, or bored.

According to various embodiments, the method may further include determining control data for controlling the at least one light source based on the at least one of mental state or motor state.

According to various embodiments, the user data may include or may be or may be included in control data for controlling the at least one light source.

According to various embodiments, the display device may include or may be or may be included in a wearable device.

According to various embodiments, the wearable device may include or may be or may be included in at least one of a wrist band or a watch.

According to various embodiments, the display device may include or may be or may be included in a peripheral device.

According to various embodiments, the peripheral device may include or may be or may be included in at least one of a mouse, a keyboard, a game controller, a headset device, a speaker device, a headset device, a head mounted device, a virtual reality device, or an augmented reality device.

According to various embodiments, the user data may be received using at least one of a wired interface, a wireless interface, a Bluetooth interface, a ZigBee interface, an infrared interface, a wireless local area network interface, a Universal Serial Bus interface, or a Thunderbolt interface.

According to various embodiments, the at least one light source may include or may be at least one colored light source. According to various embodiments, the method may further include controlling a color of the at least one light source based on the user data.

According to various embodiments, EEG (electroencephalography) data may be collected via EEG sensors mounted on an EEG headset or a similar device and may be analyzed to understand the mental state of the person. The raw EEG data may be processed to determine if the subject is for example meditative (for example calm), attentive (for example focused), winking, blinking, smiling, frowning, clenching, laughing, smiling, excited, frustrated, and/or bored.

According to various embodiments, EEG (electroencephalography) data collected from non-invasive sensors of a BCI (brain-computer interface) headset worn by a user may be used. A remote device with a light source or a plurality of light sources (for example with LEDs) that is or are wirelessly connected to the BCI headset may reflect a specific color to indicate a state of mind of the user (e.g., excited, focused, calm, bored, etc.). The remote device may be an input device (such as our Chroma mouse and keyboard, wearable device) that may change colors according to the mood of the user wearing the BCI headset.

According to various embodiments, game developers may incorporate into games a mental state of a gamer either as an integral part of the game or as a purely aesthetic effect that can be viewed by a much larger audience (for example when games are live-streamed).

According to various embodiments, EEG data may drive an input device (for example a Chroma input device) to provide smart lighting effects that may sense the mood of the user.

According to various embodiments, an individual or team members' behavior may be analyzed through wearable devices that indicate mental states. The mental states of the individual and entire teams may be observed on their wearable devices as they progress through their task or games. This may be used for studying intra group and inter group dynamics.

According to various embodiments, a color (or a plurality of colors) of the light source (or plurality of light sources; for example LEDs) mounted on the EEG headset, wearable or peripheral device may be modified according to the mental state of the subject. For example, if the subject is calm, a soothing blue may be shown on the light sources. If the person is angry or excited, the colors can be changed to a fiery red.

According to various embodiments, the EEG data may be analyzed using the processing power in the headset itself to arrive at the mental state to drive the LEDs. In this case, the algorithms processing the EEG data may be running on the headset itself.

According to various embodiments, the raw EEG data may be sensed by the headset and transmitted to another computing device like a computer or a mobile phone. The raw EEG data may be processed on this external computing device to determine the mental state of the subject. The external device may then send the result of the processing back to the headset (or any other device). The headset may then display the colors on the LEDs accordingly. How and what to display (for example colors, patterns, etc.) may be determined either by the device worn (for example headset, wristband, watch, etc.) or by the external computing device.

According to various embodiments, raw EEG data may be processed to determine mental state in a headset and/or in an external computing device (for example a PC (personal computer) or a mobile phone).

According to various embodiments, display color and/or pattern may be determined based on mental state in a headset and/or in an external computing device (for example a PC (personal computer) or a mobile phone).

According to various embodiments, the color (or color pattern) may be displayed in a headset and/or in another device (for example a wristband, a watch, a mouse, or a keyboard).

According to various embodiments, the lighting effect may be achieved via LEDs. According to various embodiments, the same effect may be obtained by any LED equivalent device, for example a keyboard backlight.

According to various embodiments, EEG data may be used to drive smart lighting effects (for example Chroma Effect on a Razer device).

According to various embodiments, people looking at the subject may immediately understand the subject's mental state by looking directly at the person. It may be easier to co-relate facial expression, body language and mental state. Without this, the person looking at the subject would have to keep switching his view between the computer display and the subject.

According to various embodiments, with the LED lighting, a large audience may see the results (for example the processed EEG, for example the derived mental state).

According to various embodiments, it may be possible to quickly observe the mental states of a group of people. Thus, multiple teams of subjects wearing the EEG headsets may be given a task (or multiple tasks). The mental states of the individual and entire teams may be quickly observed as they progress through their task or games. This may be used for studying Intra group and inter group dynamics.

According to various embodiments, a light source (for example LED display) may be provided on a PC (personal computer), on an input device (for example a keyboard or a mouse), and/or on a wearable.

According to various embodiments, EEG computations may be running on a PC and/or mobile phone and/or headset.

Various embodiments may be used during gaming or for a study of group dynamics.

According to various embodiments, raw EEG data, computed mental states and LED patterns may be transmitted over wired and wireless channels.

According to various embodiments, a mental state of a subject may be displayed on a headset, on a wearable and/or on a peripheral. In other words, an outcome of EEG processing may be displayed on the human body (for example via a wearable device) or on a peripheral device (for example mouse, keyboard, or game controller).

According to various embodiments, light sources (for example LEDs) may be used to indicate a mental state of a subject. According to various embodiments, the light sources may be embedded on a headset. According to various embodiments, the light sources may be mounted on a wearable device (e.g. wrist band or wrist watch). According to various embodiments, the light sources may be provided on a peripheral device like a mouse, keyboard, or game controller.

Various embodiments may be used in EEG headsets, audio headsets, VR (virtual reality) headsets, wearable devices (for example wrist bands or watches), peripherals (for example mice, keyboards, game controllers, or broadcasters), or computing systems (for example with lighting effect on build in keyboards, etc.).

The following examples pertain to further embodiments.

Example 1 is a display device comprising: a receiver configured to receive user data based on an electroencephalography measurement; at least one light source; and a controller configured to control the at least one light source based on the user data.

In example 2, the subject-matter of example 1 can optionally include that the user data comprises raw electroencephalography measurement data.

In example 3, the subject-matter of example 2 can optionally include a mental state determination circuit configured to determine at least one of a mental state or a motor state based on the raw electroencephalography measurement data.

In example 4, the subject-matter of example 3 can optionally include that the at least one of mental state or motor state comprises at least one of meditative, calm, attentive, focused, winking, blinking, smiling, frowning, clenching, laughing, smiling, excited, frustrated, or bored.

In example 5, the subject-matter of any one of examples 3 to 4 can optionally include a control data determination circuit configured to determine control data for controlling the at least one light source based on the at least one of mental state or motor state.

In example 6, the subject-matter of any one of examples 1 to 5 can optionally include that the user data comprises data indicating at least one of a mental state or a motor state.

In example 7, the subject-matter of example 6 can optionally include that the at least one of mental state or motor state comprises at least one of meditative, calm, attentive, focused, winking, blinking, smiling, frowning, clenching, laughing, smiling, excited, frustrated, or bored.

In example 8, the subject-matter of any one of examples 6 to 7 can optionally include a control data determination circuit configured to determine control data for controlling the at least one light source based on the at least one of mental state or motor state.

In example 9, the subject-matter of any one of examples 1 to 8 can optionally include that the user data comprises control data for controlling the at least one light source.

In example 10, the subject-matter of any one of examples 1 to 9 can optionally include that the display device comprises a wearable device.

In example 11, the subject-matter of example 10 can optionally include that the wearable device comprises at least one of a wrist band or a watch.

In example 12, the subject-matter of any one of examples 1 to 11 can optionally include that the display device comprises a peripheral device.

In example 13, the subject-matter of any one of examples 1 to 12 can optionally include that the peripheral device comprises at least one of a mouse, a keyboard, a game controller, a headset device, a speaker device, a headset device, a head mounted device, a virtual reality device, or an augmented reality device.

In example 14, the subject-matter of any one of examples 1 to 13 can optionally include that the receiver comprises at least one of a wired interface, a wireless interface, a Bluetooth interface, a ZigBee interface, an infrared interface, a wireless local area network interface, a Universal Serial Bus interface, or a Thunderbolt interface.

In example 15, the subject-matter of any one of examples 1 to 14 can optionally include that the at least one light source comprises at least one colored light source; and wherein the controller is configured to control a color of the at least one light source based on the user data.

Example 16 is a method for controlling a display device, the method comprising: receiving user data based on an electroencephalography measurement; and controlling at least one light source of the display device based on the user data.

In example 17, the subject-matter of example 16 can optionally include that the user data comprises raw electroencephalography measurement data.

In example 18, the subject-matter of example 17 can optionally include determining at least one of a mental state or a motor state based on the raw electroencephalography measurement data.

In example 19, the subject-matter of example 18 can optionally include that the at least one of mental state or motor state comprises at least one of meditative, calm, attentive, focused, winking, blinking, smiling, frowning, clenching, laughing, smiling, excited, frustrated, or bored.

In example 20, the subject-matter of any one of examples 18 to 19 can optionally include determining control data for controlling the at least one light source based on the at least one of mental state or motor state.

In example 21, the subject-matter of any one of examples 16 to 20 can optionally include that the user data comprises data indicating at least one of a mental state or a motor state.

In example 22, the subject-matter of example 21 can optionally include that the at least one of mental state or motor state comprises at least one of meditative, calm, attentive, focused, winking, blinking, smiling, frowning, clenching, laughing, smiling, excited, frustrated, or bored.

In example 23, the subject-matter of any one of examples 21 to 22 can optionally include determining control data for controlling the at least one light source based on the at least one of mental state or motor state.

In example 24, the subject-matter of any one of examples 16 to 23 can optionally include that the user data comprises control data for controlling the at least one light source.

In example 25, the subject-matter of any one of examples 16 to 24 can optionally include that the display device comprises a wearable device.

In example 26, the subject-matter of example 25 can optionally include that the wearable device comprises at least one of a wrist band or a watch.

In example 27, the subject-matter of any one of examples 16 to 26 can optionally include that the display device comprises a peripheral device.

In example 28, the subject-matter of any one of examples 16 to 27 can optionally include that the peripheral device comprises at least one of a mouse, a keyboard, a game controller, a headset device, a speaker device, a headset device, a head mounted device, a virtual reality device, or an augmented reality device.

In example 29, the subject-matter of any one of examples 16 to 28 can optionally include that the user data is received using at least one of a wired interface, a wireless interface, a Bluetooth interface, a ZigBee interface, an infrared interface, a wireless local area network interface, a Universal Serial Bus interface, or a Thunderbolt interface.

In example 30, the subject-matter of any one of examples 16 to 29 can optionally include that the at least one light source comprises at least one colored light source; and wherein the method further comprises controlling a color of the at least one light source based on the user data.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A keyboard comprising:
a receiver, the receiver of the keyboard configured to receive an electroencephalography measurement data of a user playing a game;
a backlight comprising at least one light source; and
a controller configured to control the at least one light source of the backlight of the keyboard based on the electroencephalography measurement data of the user, as the user progresses through the game.

2. The keyboard of claim 1, further comprising:
a mental state determination circuit configured to determine at least one of a mental state or a motor state based on the electroencephalography measurement data.

3. The keyboard of claim 2, further comprising:
a control data determination circuit configured to determine control data for controlling the at least one light source based on the at least one of mental state or motor state.

4. The keyboard of claim 1,
wherein the electroencephalography measurement data comprises data indicating at least one of a mental state or a motor state.

5. The keyboard of claim 4, further comprising:
a control data determination circuit configured to determine control data for controlling the at least one light source based on the at least one of mental state or motor state.

6. The keyboard of claim 1,
wherein the receiver comprises at least one of a wired interface, a wireless interface, a Bluetooth interface, a ZigBee interface, an infrared interface, a wireless local area network interface, a Universal Serial Bus interface, or a Thunderbolt interface.

7. The keyboard of claim 1,
wherein the at least one light source comprises at least one colored light source; and
wherein the controller is configured to control a color of the at least one light source based on the electroencephalography measurement data.

8. The keyboard of claim 1,
wherein the controller is configured to control a light intensity of the at least one light source based on the electroencephalography measurement data.

9. The keyboard of claim 2,
wherein the mental state determination circuit of the keyboard is configured to determine whether the user is feeling calm or frustrated; and
wherein the controller of the keyboard is configured to control the at least one light source of the backlight of the keyboard according to a first manner when it is determined that the user is feeling calm and according to a second manner, different from the first manner, when it is determined that the user is feeling frustrated, as the user progresses through the game, thereby enabling the mental state of the user to be observable from the keyboard as the user progresses through the game.

10. The keyboard of claim 9,
wherein the first manner comprises controlling the at least one light source of the backlight of the keyboard to emit a blue colored light when the user is determined to be feeling calm and the second manner comprises controlling the at least one light source of the backlight of the keyboard to emit a red colored light when the user is determined to be feeling frustrated.

11. The keyboard of claim 9,
wherein the first manner comprises controlling the at least one light source of the backlight of the keyboard to emit light according to a first pattern and the second manner comprises controlling the at least one light source of the backlight of the keyboard to emit light according to a second pattern.

12. A method for controlling a keyboard comprising a backlight comprising at least one light source, the method comprising:
receiving an electroencephalography measurement data of a user playing a game; and
controlling at least one light source of the backlight of the keyboard based on the electroencephalography measurement data of the user, as the user progresses through the game.

13. The method of claim 12, further comprising:
determining at least one of a mental state or a motor state based on the electroencephalography measurement data.

14. The method of claim 13, further comprising:
determining control data for controlling the at least one light source based on the at least one of mental state or motor state.

15. The method of claim 12,
wherein the electroencephalography measurement data comprises data indicating at least one of a mental state or a motor state.

16. The method of claim 15, further comprising:
determining control data for controlling the at least one light source based on the at least one of mental state or motor state.

17. The method of claim 12,
wherein the electroencephalography measurement data is received using at least one of a wired interface, a wireless interface, a Bluetooth interface, a ZigBee interface, an infrared interface, a wireless local area network interface, a Universal Serial Bus interface, or a Thunderbolt interface.

18. The method of claim 12,
wherein the at least one light source comprises at least one colored light source; and wherein the method further comprises controlling a color of the at least one light source based on the electroencephalography measurement data.

19. A system comprising:
a first keyboard comprising:
   a first receiver, the first receiver of the first keyboard configured to receive a first user data based on an electroencephalography measurement of a first user playing a game,
   a first backlight comprising at least one light source, and
   a first controller configured to control the at least one light source of the first backlight of the first keyboard based on the first user data of the first user, as the first user progresses through the game; and
a second keyboard comprising:
   a second receiver, the second receiver of the second keyboard configured to receive a second user data based on an electroencephalography measurement of a second user playing the game that is also being played by the first user with the first keyboard,
   a second backlight comprising at least one light source, and
   a second controller configured to control the at least one light source of the second backlight of the second keyboard based on the second user data of the second user, as the second user progresses through the game;
whereby the first and the second user data of the first and second users are simultaneous communicated by the first and the second keyboards via the first and second backlights, as the first and the second users simultaneously progress through the game.

* * * * *